United States Patent [19]

Banik et al.

[11] 4,123,510

[45] Oct. 31, 1978

[54] METHOD FOR THE DETERMINATION OF GONADOTROPINS

[75] Inventors: Upendra K. Banik; Morris L. Givner, both of Pierrefonds, Canada

[73] Assignee: American Home Products Corp. (Del.), New York, N.Y.

[21] Appl. No.: 806,569

[22] Filed: Jun. 14, 1977

Related U.S. Application Data

[63] Continuation-in-part of Ser. No. 786,721, Apr. 11, 1977, which is a continuation-in-part of Ser. No. 534,400, Dec. 19, 1974, abandoned.

[51] Int. Cl.² .................. B01D 13/00; G01N 1/00; G01N 31/00; G01N 33/16
[52] U.S. Cl. .................. 424/12; 23/230 B; 210/22 R; 210/23 F; 424/99; 424/100; 424/101; 424/108
[58] Field of Search ........... 210/DIG. 23, 23 F, 22 R; 424/8, 12, 99, 100, 101, 108; 23/230 B, 259

[56] References Cited

U.S. PATENT DOCUMENTS

| | | | |
|---|---|---|---|
| 3,485,751 | 12/1969 | Hermann | 210/22 |
| 3,488,768 | 1/1970 | Rigopulos | 210/380 X |
| 3,817,379 | 6/1974 | Zipilivan | 210/94 |
| 3,991,174 | 11/1976 | Grundman | 424/12 |
| 4,033,723 | 7/1977 | Givner | 210/23 F |

FOREIGN PATENT DOCUMENTS 126,454  3/1968  Czechoslovakia .................. 424/12

OTHER PUBLICATIONS

Vierneisel, Chem. Abs., vol. 59, 1963, pp. 14255d.
Orlandi, Chem. Abs., vol. 62, 1965, pp. 8079b.
Taymor, J. Endocrinol., vol. 36, 1966, pp. 417–418, 1 plate.
Vaitukaitis, J. Clin. Endocrin., vol. 33, 1971, pp. 988–991.
Franchimont, Proc. Int. Symp. Protein & Polypeptide Hormones Excerpta Med. Found., 1967, pp. 381, 383–387.
Fine, AJCP, vol. 49, 1968, pp. 171–182.
Lok, Asian J. of Med., vol. 9, Sep. 1973, pp. 319–320.
Curtiss, J. of Virology, vol. 14, Sep. 1974, pp. 503–504.
Wide, Acta Endocrin., Supp. vol. 70, 1962, pp. 68–74.
Killip, AJCP, vol. 61, Mar. 1974, pp. 337–340.
Wagner, Acta Endocrin. Supp., vol. 31, 1957, pp. 90–99.
Lysaght, ACS Meeting, Apr. 1–5, 1974, vol. 34, No1., Coatings & Plastics Preprints of Papers, pp. 578–581.
Amicon Corp. Sci. System Div. Pre-Concentration & Deprot. in the Clin. Lab., Applications Guide, Pub. No. 434, May 1973, pp. 1–7.
Tamada, J. Clin. Endocrin, vol. 27, Mar. 1967, pp. 379–384.
Edwards, Physiol. Effects of Immunity Against Reproductive Hormones, Cambridge U. Press, London, Clin. & Exptl. Immunoreproduction, vol. 3, 1976, pp. 23–32.
Hobson, J. Reprod. Fert., vol. 12, 1966, pp. 33–48.
Jame, Path.–Biol., vol. 19, No. 23–24, 1971, pp. 1115–1119.

*Primary Examiner*—Anna P. Fagelson
*Attorney, Agent, or Firm*—Adley F. Mandel

[57] ABSTRACT

A simple, sensitive, reliable and safe method for determining the concentration of pituitary gonadotropins is disclosed. The method involves concentration by ultrafiltration of a sample of body fluid, e.g. urine or serum from a subject, followed by determining the presence of the gonadotropin in the concentrated sample.

12 Claims, No Drawings

METHOD FOR THE DETERMINATION OF GONADOTROPINS

This application is a contnuation-in-part of Ser. No. 786,721, filed Apr. 11, 1977, pending which is a continuation-in-part of Ser. No. 534,400 filed Dec. 19, 1974, now abandoned.

SUMMARY OF THE INVENTION (a) Field of the Invention

This invention relates to a method for determining pituitary gonadotropins in body fluids. More specifically, this invention concerns a simple and sensitive method for determining levels of luteinizing hormone, follicle-stimulating hormone or human menopausal gonadotropin.

(b) Prior Art

Although a variety of methods are available for the determination of pituitary gonadotropins in body fluid, they usually lack one or more of the following advantages: reliability, sensitivity, simplicity or speed. In this respect a method having these advantages would be a valuable asset to medicine since it would provide a ready assessment of pituitary function and would indicate ovulation and estrogen secretion.

Ovulation is the central event in a normal biphasic ovarian cycle. The rupture of the mature follicle occurs 16 to 24 hours after the beginning of the midcycle surge of luteinizing hormone (LH), G. T. Ross and R. L. Vande Wiele in "Textbook of Endocrinology," 5th ed., R. H. Williams, Ed., W. B. Saunders Co., Philadelphia, U.S.A., 1974, pp. 368–422. Before ovulation the concentration of LH in urine is about 6 to 25 m.I.U./ml. The concentration rises to a peak of about 25 to 600 m.I.U./ml at ovulation. See A. H. W. M. Schuurs and C. J. van Wijngaarden, Acta Endocrinol., Suppl. 141, 13 (1970); D. McEvoy et al, a presentation made at the 8th International Congress of Clinical Chemistry, Copenhagen, 1972; R. Vande Wiele, Hospital Practice, 10, 119 (1972); K. Thomas and J. Ferin, Acta Endocrinol., Suppl. 141, 75 (1970); L. Grundman, U.S. Pat. No. 3,991,174, issued Nov. 9, 1976; S. Donni and P. Donni, Karolinska Symposium On Research Method In Reproductive Endocrinology, 1st Symposium, Immunoassay of Gonadotropins, September 23–25, 1969, pp. 257–278; and Institute of Bio-Endocrinology, Clinical Chemistry, 23, 425, (1977).

Despite much effort there is still no absolutely reliable and simple method for determining the time of ovulation. Under exceptional circumstances ovulation can be visualized during culdoscopy, culdotomy or laparatomy. Ovulation may be indicated indirectly by increased LH concentration in body fluids (i.e., serum or urine), basal body temperature, endometrial biopsy, urinary pregnanediol, cervix factor, vaginal cytology, or clinical symptoms.

A method for estimating the level of LH in body fluids would appear to offer the most promise for developing a simple and reliable method for detecting ovulation. Indeed a number of methods are available but they do have drawbacks. For example, an immunological test method sold commercially under the name "Luteonosticon"* and a recent immunological method described in U.S. Pat. No. 3,991,174, issued November 9, 1976, are complicated methods, requiring much equipment and time. In addition, the methods use small volumes of urine, the LH content of which is susceptible to losses and unreliable estimations. Non-specific radioimmunoassay (RIA) techniques have been used for determining LH concentrations in body fluid, for example see R. B. Jaffe, et al., J. Clin. Endocrinol. Metabol., 29, 1281 (1969). Although RIA techniques are sensitive, these methods are expensive and complex. They must be performed by highly trained personnel using isotopic material and very sophisticated equipment.

* Trademark

Similar consideration apply to the need for a simple and reliable method for determining follicle-stimulating hormone (FSH) and human menopausal gonadotropin (HMG). It is well known that fluctuations of normal levels of the gonadotropins indicate hypothalamic, pituitary or gonadal dysfunction; see S. Chakravarti, et al., British Medical Journal, 784 (1976) and references therein. For example, estrogen deficiency in menopausal women is indicated usually by the rise of FSH levels in serum from a normal range of about 15 m.I.U./ml to levels ranging from about 40 to 250 m.I.U./ml, see Chakravarti, cited above and references cited therein and R. S. Swerdloff and W. D. Odell, California Medicine, 109, 467 (1968). However, methods for detecting FSH and HMG levels using immunological and radio-immunological assays have the same drawbacks as mentioned above for the LH methods.

The present invention, therefore, fulfills a need by providing a convenient and reliable method for detecting gonadotropins of pituitary origin.

SUMMARY OF THE INVENTION

According to one aspect of the present invention, a simple and sensitive method for detecting levels of a pituitary gonadotropin in a body fluid of a subject is effected by a process, comprising:
(a) concentrating the body fluid by ultrafiltration through a membrane having a molecular cut-off rendering the membrane impermeable to the gonadotropin to obtain a retentate of the fluid, and
(b) contacting the retentate with an immunological reagent for detecting the presence of the gonadotropin.

A preferred embodiment of the above method the body fluid is urine and includes the step of clarification of the urine sample by filtration or centrifugation prior to concentration.

Another embodiment of this invention relates to a method suitable for the detection of luteinizing hormone (LH) in urine at a concentration as low as about 25 m.I.U./ml of urine and capable of detecting ovulation in a cycling woman, which comprises:
(a) clarifying a sample of the urine to be tested;
(b) contacting the urine sample before, during or after clarification with 0.1 to 5% aqueous solution of a protein so that adsorption of LH from the sample onto the membrane is substantially reduced;
(c) subjecting about 5 to 50 ml of the clarified urine sample to ultrafiltration through an ultrafiltration membrane having a molecular weight cut-off from about 5,000 to about 50,000, whereby LH is retained in the sample;
(d) continuing the ultrafiltration until the retentate sample is one-tenth to one-five hundredth its original volume;
(e) diluting the retentate sample with sufficient water to provide a retentate sample of about 0.5 ml; and
(f) contacting the retentate sample with the appropriate amount of an immunological reagent for detecting the presence of LH in the retentate sample.

Still another embodiment of this invention relates to a method for detecting follicle-stimulating hormone (FSH) or human menopausal gonadotropin (HMG) in urine at a concentration of 15 or more m.I.U./ml of urine, which comprises:

(a) clarifying a sample of the urine to be tested;
(b) contacting the urine sample before or after clarification with 0.1 to 5% aqueous solution of a protein so that adsorption of FSH or HMG from the sample onto the membrane is substantially reduced;
(c) subjecting about 5 to 50 ml of the clarified urine sample to ultrafiltration through an ultrafiltration membrane having a molecular weight cut-off from about 5,000 to about 50,000, whereby FSH or HMG is retained in the sample;
(d) continuing the ultrafiltration until the retentate sample is one-tenth to one-five hundredth its original volume;
(e) diluting the retentate sample with sufficient water to provide a retentate sample of about 0.5 ml; and
(f) contacting the retentate sample with the appropriate amount of an immunological reagent for detecting the presence of FSH or HMG in the retentate sample.

DETAILS OF THE INVENTION

The term "molecular cut-off" as used herein refers to the capacity of an ultrafiltration membrane to retain 80 to 100% of those molecules having a molecular weight equal to or greater than the number associated with the term, while allowing those molecules of lesser molecular weight to pass through the membrane.

The term "immunological reagent" includes reagents used to perform an agglutination test, or an agglutination inhibition test. In these tests red blood cell or latex particles may be used.

The first step of the gonadotropin detection method of this invention involves filtering the urine or serum sample and concentrating the filtered sample by ultrafiltration using a suitable ultrafiltration membrane. In the case of the concentration of urine, preferably a sample from the first morning urination is used. A number of such ultrafiltration membranes are described by W. F. Blatt in "Methods in Enzymology," Vol. XXII, W. B. Jakoby, Ed., Academic Press, New York and London, 1971; V. E. Pollak, et al., J. Lab. Clin. Med., 71, 388 (1968); W. F. Blatt et al., Nature, 216, 511 (1967) and W. F. Blatt., et al., Science, 150, 224 (1965); as well as in U.S. Pat. No. 3,549,016, issued Dec. 22, 1970; and U.S. Pat. No. 3,615,024, issued Oct. 26, 1971.

Examples of suitable ultrafiltration membranes include those of anisotropic, aromatic polymer type, for instance Diaflo PM-10*, Diaflo PM-20*, and Diaflo PM-30* (Amicon Corp); Iopor AP* and Lopor XP* (Dorr-Oliver, Stamford, Conn.); the anisotropic, cellulosic type, for instance, HFA-100 and HFA-200 (Abcor Inc., Cambridge, Mass.) and PSED (Millipore Corp., Bedford., Mass.); and gel cellophane such as manufactured by du Pont Chemicals, Wilmington, Delaware or Union Carbide, N.Y.C.

*Trademark

Methods and apparatus for concentration by ultrafiltration of the aforementioned sample are described in the above references pertaining to ultrafiltration membranes. Particularly useful designs for ultrafiltration concentrators are described also by E. M. Zipilivan, et al., in U.S. Pat. No. 3,817,379, issued June 18, 1974. This reference is herein incorporated in its entirety by reference.

In addition, U.S. Application, Ser. No. 645,860, filed Dec. 31, 1975 of Givner and Schilling, now U.S. Pat. No. 4,033,723, herein incorporated by reference, discloses a device suitable for the method of this invention. The device includes a chamber, opened at the top and closed at the bottom, having the upper portion of at least one wall formed of an ultrafiltration membrane permeable to body fluid, e.g. urine or serum, and capable of selective retention of a gonadotropin, all other walls being formed of a rigid impermeable material, and a layer of absorbent capable of absorbing urine or serum passing through the membrane, the absorbent being contiguous to the outside surface of the membrane and in effective contact with the membrane. The chamber further includes a lower portion, all walls of which are impermeable, for retaining a fixed volume of urine or serum concentrate containing the gonadotropin, outlet means in the lower portion of the chamber, means for opening the outlet means, and a reagent receptacle connected to the chamber through the outlet means, the reagent receptacle adapted to receive a reagent for the immunological determination of the gonadotropin and means for viewing the reaction of the reagent therein with the said urine or serum concentrate.

An embodiment of the preceding device includes a filter disposed for filtering urine being introduced into the chamber.

Thereafter, the present method involves the detection of the pituitary gonadotropin in the concentrated sample. Preferred test methods for determining the presence of the gonadotropin in the concentrated urine or serum sample are the tests using immunological reagents.

Suitable immunological reagents include any of the known antisera which react serologically with the pituitary gonadotropin to be detected. One can employ a specific antiserum to the gonadotropin or any known anti-human chorionic gonadotropin (HCG) serum provided that it cross reacts with the gonadotropin, i.e. LH, FSH or HMG, to be detected. Examples of suitable immunological reagents are described in co-pending Application AHP-6522, Hirsch, Irvine and Krupey, filed of even date herewith, incorporated herein by reference, and as follows:

Reagents comprising the antigens, LH, FSH, or HMG, including synthetic or natural subunits or fragments chemically or enzymatically prepared thereof, and antisera derived therefrom, e.g., anti-LH, N. R. Moudgal and H. G. Madwa Raj, Pituitary Gonadotropins in "Methods of Hormone Radioimmunoassay," B. M. Jaffe and H. R. Behrman, Ed., Academic Press, New York, 1974, page 75; anti-FSH, A. H. W. M. Schuurs and C. J. van Wijngaarden, J. Clin. Endocrinol. Metabol., 40. 619 (1975); and anti-HMG, B. Lunefeld, et al., J. Clin. Endocrinol. Metabol., 21, 478 (1961).

In addition, suitable reagents commonly used for the detection of HCG in pregnancy can be used provided that the antisera contained therein cross reacts serologically with the pituitary gonadotropins. Suitable reagents are those employed in the following tests.

The agglutination tests, for example see H. Fink and A. Frie, Obstet. Gynecol., 28, 660 (1966), are based on the direct reaction between HCG and a HCG-antibody.

The agglutination inhibition tests are based on an inhibition of a reaction between HCG-antiserum and HCG on a carrier, for instance, red blood cells or latex particles. When the latter test involves red blood cells it is known as the haemagglutination inhibition test and when the latter test involves particles it is known as the latex agglutination inhibition test. For example, see L. Wide and C. A. Gemzell, Acta Endocrinol., 35. 26; (1960); B. M. Hodson, J. Reprod. Fert., 12, 33 (1966) and references cited therein; B. M. Hibbard, Brit. Med. J., I, 593 (1971); U.S. Pat. No. 3,548,051, issued Dec. 15, 1970; U.S. Pat. No. 3,551,555, issued Dec. 29, 1970; and U.S. Pat. No. 3,666,421, issued May 30, 1972.

The HCG-antibody, required for the above tests, is known. The preparation of the antibody has been described several times, for example, see Wide and Gemzell, cited above, and A. R. Midgley, et al., Proc. Soc. Exp. Biol. Med., 108, 85 (1961).

The sensitivity of the test is a function of the concentration of the active immunologic reagent. For the present method the sensitivity of the reagent is predetermined so that a positive reaction with LH results when it is present in the urine or serum at a concentration of 25 m.I.U./ml. For example in the haemagglutination inhibition test the active immunological reagent is adjusted so that haemagglutination is inhibited at 25 m.I.U./ml of LH in the body fluid which may be immunologically equivalent to approximately 10 m.I.U./ml of HCG. Similar considerations apply to predetermining the sensitivity of the reagents for the detection of FSH or HMG at 15 m.I.U./ml, see below. Method for adjusting the sensitivity of the reagents are well known; for example, see E. A. Kabat and M. M. Mayer in "Experimental Immunochemistry," 2nd ed., Charles C. Thomas Publisher, Springfield, Ill., U.S.A., 1961, pp. 97–132; and L. Wide, Acta Endocrinol., Suppl. 70, 20–27 (1962).

Test kits suitable for the detection of the pituitary gonadotropin in urine and serum samples according to the method of this invention are available commercially; for example, the haemagglutination inhibition test kits, for instance, Pregnosticon All-in* (Organon, Holland and U.S.A.) and UCG* (Wampole Laboratories, Stamford, Conn.); latext agglutination inhibition test kits, for instance, Planotest*, Pregnosticon Dri-Dot* (Organon, Holland and U.S.A.), Gravindex* (Ortho, Raritan, N.J., U.S.A.) and Prepurex* or Prepurin* (Burroughs Wellcome, U.S.A. and United Kingdom); and the direct agglutination test, for instance, DAP Test (Denver Biologicals Co. U.S.A.) and Gonavislide (Molter Cmbh., West Germany).
*Trademark If desired, urine samples or retentates of urine samples containing high concentration of LH, FSH or HMG may be serially diluted prior to addition to the immunologic reagent for a more accurate estimation of gonadotropin levels.

More specifically, in practising the method of this invention for detecting the presence of LH, a sample of female urine or serum, the urine preferably being clarified by filtration through a suitable filter paper or by centrifugation, is concentrated 10 to 500 times, preferably 10 to 50 times by placing the sample in contact with an ultrafiltration membrane having a molecular weight cut-off ranging from about 5,000 to about 50,000, preferably about 10,000 to 35,000. In other words, a lower limit of 5,000 or preferably 15,000 and an upper limit of 50,000, preferably an upper limit of 35,000, have been found useful. The sample is filtered through the membrane until the unfiltered portion of the sample (retentate) has reached the desired degree of concentration. The concentration step is carried out usually at temperatures ranging from about 0° to 40° C, preferably 4° to 25° C, and usually takes half an hour to two hours. For convenience in performing the immunological test, the retentate is diluted with sufficient water to provide a retentate sample of about 0.5 ml if the retentate is less than this volume. Thereafter, the retentate is subjected to an immunological test for the presence of LH according to one of the methods mentioned above.

The aqueous solution of the concentrated urine or serum is mixed in an ampoule-tube or on a slide with the regularly recommended amount of a lyophilized mixture of LH-antiserum or HCG-antiserum, erythrocytes or latex particles sensitized with LH or HCG, buffer, preservatives and excipients.

In the case of the tube test, (e.g. haemagglutination inhibition test) after allowing the mixture to stand for about one to two hours, a positive reaction is indicated by a specific sedimentation pattern in the form of a clearly defined ring at the bottom of the tube. A negative reaction is indicated by a diffuse yellow-brown sediment.

Alternatively, latex agglutination inhibition or direct agglutination tests, with their characteristic visual end-points, see above for details, are used for the detection of LH in the aqueous solution of concentrated urine.

In a preferred modification of the above noted practice of this invention, it has been found advantageous to subject the inner surface of the concentrator, i.e., the chamber containing the ultrafiltration membrane, to a prewash with a 0.1 to 5%, preferably 0.1 to 1.0% aqueous solution of bovine serum albumin (BSA), to contact the inner surfaces of the concentrator prior to placing the sample of urine in the concentrator. This modification significantly improves the sensitivity of the present method by preventing absorption losses of the gonadotropin on the surface of the device (thereby increasing the sensitivity of the method) and improves the replication of the test. The latter aspect is of paramount importance when only single tests are performed.

Furthermore, it has been found that the same advantageous results are obtained if the BSA solution is used to wash the aforementioned filter paper used to filter the urine or serum sample or if BSA is added directly to the initially collected urine sample to give a concentration ranging from 0.001 to 1.0% preferably 0.01 to 1.0% BSA in the urine.

Proteins other than BSA also are suitable for the aforementioned purpose; the filter paper, urine or inner surface of the ultrafiltration membrane can be treated with such a protein so that adsorption of LH from the sample to the filter paper or to the inner surfaces of the concentrator, including the ultrafiltration membrane, is substantially reduced. Examples of suitable proteins are human serum albumin, rabbit serum albumin, egg albumin, gamma globulin (both bovine and human), myoglobin, fibrogen, human hemoglobin and keyhole limpet hemocyanin.

Although it may appear obvious to concentrate a dilute solution of a gonadotropin so that the concentration of the gonadotropin falls within the sensitivity range of a given test, it is in direct contradiction to the cumulative experience with immunological test since it will be appreciated that concentration of such body fluids as urine and serum likewise concentrates those substances which may interfere with the immunological test.

In one exemplified embodiment of the method of this invention, concentration of a urine sample is effected by the use of a Minicon-B-15* ultrafiltration concentrator supplied by Amicon Corporation, Lexington, Massachusetts, U.S.A. According to the manufacturer the Minicon-B-15 concentrator is based on the principle of backing an anisotropic Diaflo* ultrafiltration membrane having a molecular cut-off of 15,000, with absorbent pads. Concentrators of this particular design are described in U.S. Pat. No. 3,817,379, cited above.
*Trademark With reference to the present embodiment, a five ml. sample of first voided morning urine, filtered through Whatman No. 1 filter paper, was concentrated by placing the sample in a well of the Minicon-B-15* concentrator. During the concentration step the concentrator was allowed to stand in an ambient temperature of about 22° C. i.e. room temperature. After a period of about one to two hours the sample had concentrated to about 0.1 ml. The concentrated urine (retentate) was removed from the concentrator and diluted back to a volume of 0.5 ml with distilled water to give the aqueous solution of the concentrated urine. Removal of the retentate was done by using a fine Pasteur pipette. Thereafter, the aqueous solution of the concentrated urine was tested for the presence of LH by a haemagglutination inhibition test. In this instance, the Pregnosticon Allin* test kit (used to detect the HCG in pregnancy) was employed. The HCG antisera in this immunological reagent is non-specific for HCG and cross reacts with LH.
*Trademark After one to two hours (tube test), a reading is made and if a specific sedimentation pattern in the form a clearly defined ring, depending on the shape of the bottom of the test kit receptacle, i.e., round-bottom, then ovulation has occurred. If no ring appears, ovulation may not have taken place or has already occurred.

Tables IA to ID list the results from a comparative study in which various means were used to detect ovulation in normal cycling women. The methods used were the daily measurements of basal body temperature (BBT), urinary pregnanediol excretion, plasma LH by radioimmunological assay, and the detection of increased amounts of LH in urine by the above-mentioned preferred method of this invention, performed with and without a 1% (w/v) aqueous BSA prewash of the filter paper. Note that for this study, when the method of this invention was used, the retentate (0.1 ml) was diluted back with distilled water to a volume of 0.5 ml. The diluted retentate then was added to a Pregnosticon All-in* ampoule and this test is designated UF-HIT(P).
*Trademark Table 1A

| Subject No. (age) | Days after LMP[a] | BBT[b] °C | Detection of ovulation Urinary Pregnanediol (mg/24 hr) | Plasma LH (mIU/ml) | UF-HIT(P) −BSA[c] | UF-HIT(P) +BSA[d] |
|---|---|---|---|---|---|---|
| 1 (20) | 12 | 36.5 | 0.85 | 8 | −[e] | − |
|  | 13 | 36.7 | 0.99 | 9 | − | − |
|  | 14 | 36.6 | 0.98 | 10 | − | − |
|  | 15 | 36.8 | 1.25 | 17 | − | − |
|  | 16 | 37.2 | 1.68 | 39 | − | − |
|  | 17 | 37.1 | 2.78 | 58 | ± | ± |
|  | 18 | 37.0 | 2.22 | 33 | − | − |
| 2 (19) | 12 | 36.0 | 1.50 | 10 | − | − |
|  | 13 | 36.8 | 1.69 | 18 | − | − |
|  | 14 | 36.9 | 1.99 | 37 | − | − |
|  | 15 | 37.0 | 2.78 | 39 | − | − |
|  | 16 | 37.3 | 3.84 | 70 | + | + |
|  | 17 | 37.2 | 3.88 | 65 | + | + |
|  | 18 | 37.0 | 3.91 | 45 | − | − |
| 3 (19) | 12 | ND[f] | 0.72 | 12 | − | − |
|  | 13 | 36.5 | 0.99 | 15 | − | − |
|  | 14 | 36.9 | 1.80 | 25 | − | − |
|  | 15 | 36.9 | 1.99 | 29 | − | − |
|  | 16 | 36.8 | 2.00 | 20 | − | − |
|  | 17 | 37.4 | 3.67 | 78 | + | + |
|  | 18 | 37.1 | 3.45 | 60 | − | − |

[a] Last menstrual period
[b] Basal body temperature
[c] Urine was filtered through untreated Whatman No. 1 filter paper
[d] Urine was filtered through Whatman No. 1 filter paper treated with 1% (w/v) aqueous BSA (and dried at room temperature).
[e] − = negative reaction; + = positive reaction and ± = doubtful reaction
[f] ND = not done.

Table 1B

| Subject No. (age) | Days after LMP | BBT °C | Detection of ovulation Urinary Pregnanediol (mg/24 hr) | Plasma LH (mIU/ml) | UF-HIT(P) −BSA | UF-HIT(P) +BSA |
|---|---|---|---|---|---|---|
| 3-A[a] (19) | 12 | ND | ND | ND | ND | ND |
|  | 13 | 37.1 | 1.25 | 7 | − | − |
|  | 14 | 36.9 | 1.34 | 8 | − | − |
|  | 15 | 37.0 | 1.44 | 12 | − | − |
|  | 16 | 36.6 | 1.50 | 54 | + | + |
|  | 17 | 36.9 | 2.27 | 44 | − | − |
|  | 18 | 37.3 | 5.89 | 18 | − | − |
| 4 (20) | 12 | 36.4 | 1.10 | 11 | − | − |
|  | 13 | 37.0 | 1.15 | 14 | − | − |
|  | 14 | 37.2 | 3.45 | 79 | + | + |
|  | 15 | 37.1 | 3.33 | 89 | + | + |
|  | 16 | 36.9 | 3.69 | 85 | + | + |
|  | 17 | 37.0 | 3.56 | 32 | − | − |
|  | 18 | 36.9 | 3.58 | 20 | − | − |
| 5 (21) | 12 | 36.0 | 1.10 | 6 | − | − |
|  | 13 | 36.4 | 1.17 | 10 | − | − |
|  | 14 | 36.8 | 1.19 | 99 | + | + |

Table 1B-continued

| Subject No. (age) | Days after LMP | BBT °C | Detection of ovulation Urinary Pregnanediol (mg/24 hr) | Plasma LH (mIU/ml) | UF-HIT(P) −BSA | UF-HIT(P) +BSA |
|---|---|---|---|---|---|---|
| | 15 | 37.3 | 3.87 | 33 | ± | − |
| | 16 | 36.9 | 3.90 | 25 | − | − |
| | 17 | 37.3 | 4.08 | 20 | − | − |
| | 18 | 36.9 | 4.17 | 19 | − | − |

<sup>a</sup>Successive cycle of Subject No. 3.

Table 1C

| Subject No. (age) | Days after LMP | BBT °C | Detection of ovulation Urinary Pregnanediol (mg/24 hr) | Plasma LH (mIU/ml) | UF-HIT(P) −BSA | UF-HIT(P) +BSA |
|---|---|---|---|---|---|---|
| 6 (19) | 12 | 36.5 | 2.06 | 14 | − | ND |
| | 13 | 36.6 | 2.23 | 53 | − | " |
| | 14 | 37.2 | 4.55 | 109 | + | " |
| | 15 | 37.1 | 4.06 | 44 | + | " |
| | 16 | 37.2 | 4.49 | 18 | − | " |
| | 17 | 37.1 | 4.41 | 17 | − | " |
| | 18 | 37.0 | 3.88 | 15 | − | " |
| 7 (20) | 12 | 36.3 | 1.31 | 8 | − | ND |
| | 13 | 36.5 | 1.40 | 6 | − | " |
| | 14 | 36.6 | 1.63 | 9 | − | " |
| | 15 | 36.2 | 1.80 | 5 | − | " |
| | 16 | 36.1 | 1.94 | 61 | ± | " |
| | 17 | 36.7 | 1.44 | 49 | + | " |
| | 18 | 37.4 | 3.65 | 21 | − | " |
| 8 (18) | 12 | 36.6 | 1.23 | 10 | − | − |
| | 13 | 36.2 | 0.92 | 42 | − | ± |
| | 14 | 36.6 | 0.90 | 79 | + | + |
| | 15 | 37.2 | 1.21 | 18 | − | − |
| | 16 | 37.1 | 4.24 | 20 | − | − |
| | 17 | 37.1 | 4.09 | 16 | − | − |
| | 18 | 37.0 | 4.12 | 15 | − | − |

Table 1D

| Subject No. (age) | Days after LMP | BBT °C | Detection of ovulation Urinary Pregnanediol (mg/24 hr) | Plasma LH (mIU/ml) | UF-HIT(P) −BSA | UF-HIT(P) +BSA |
|---|---|---|---|---|---|---|
| 9 (20) | 12 | 36.6 | 0.67 | 5 | − | − |
| | 13 | 36.7 | 0.72 | 7 | − | − |
| | 14 | 37.0 | 1.21 | 6 | − | − |
| | 15 | 36.0 | 1.22 | 10 | − | − |
| | 16 | 36.4 | 1.23 | 40 | ± | + |
| | 17 | 37.3 | 2.16 | 98 | + | + |
| | 18 | 37.3 | 3.09 | 51 | + | + |
| 10 (20) | 12 | 36.5 | 1.08 | 13 | − | ND |
| | 13 | 36.4 | 1.31 | 74 | − | " |
| | 14 | 36.8 | 1.44 | 89 | + | " |
| | 15 | 37.3 | 2.88 | 19 | ± | " |
| | 16 | 37.2 | 2.96 | 16 | − | " |
| | 17 | 37.1 | 3.41 | 18 | − | " |
| | 18 | 37.3 | 3.94 | 22 | − | " |
| 11 (20) | 12 | 36.8 | 1.16 | 12 | − | − |
| | 13 | 37.1 | 1.89 | 16 | − | − |
| | 14 | 37.2 | 2.25 | 76 | + | + |
| | 15 | 37.4 | 3.99 | 51 | ± | ± |
| | 16 | 37.0 | 4.96 | 32 | − | − |
| | 17 | 36.7 | 4.56 | 30 | − | − |
| | 18 | 36.5 | 4.01 | 27 | − | − |

The results in Tables 1A and 1D show an excellent agreement in detecting ovulation by the increase in LH in plasma by radioimmunoassy and in the urine by the more simple method of this invention (with or without the use of BSA). A common finding was the rise in urinary pregnanediol that is characteristic of the post ovulatory luteal phase. On the other hand, BBT readings were inadequate for the detection of ovulation. Note that testing unconcentrated daily urine samples directly with the reagent used in this study repeatedly gave a negative reaction. These results demonstrate the excellent reliability and sensitivity of the method of this invention.

Concerning the application of the method of this invention for determining estrogen deficiencies the method can be applied for detecting elevated levels of FSH or HMG in women suspected of having such a deficiency, namely women experiencing menopausal symptoms. In this situation the above described procedure and techniques for LH determination apply except that one employs as an immunological reagent an appropriate antigen and a specific antiserum for FSH or HMG or any antisera that cross reacts with these gonadotropins.

Finally in addition to being applicable for detecting ovulation and estrogen deficiency, the method of this invention is useful for detecting other manifestations of pituitary and gonadal function. For example, the method is useful to detect or to differentiate hyposecretion, normal or hypersecretion of LH, to determine LH in amenorrhea or anovulatory cycles, to assess pituitary function in precocious or delayed puberty, or to determine LH in subjects suffering from testicular failure.

We claim:
1. A method suitable for detection of luteinizing hormone in urine at a concentration as low as about 25 m.I.U./ml of urine and capable of detecting ovulation in a cycling woman, which comprises:
   (a) clarifying a sample of the urine to be tested;
   (b) contacting the urine sample before, during or after clarification with 0.1 to 5% aqueous solution of a protein selected from the group consisting of bovine serum albumin, rabbit serum albumin, human serum albumin, gamma globulin, myoglobin, fibrinogen, human hemoglobin, and keyhold limpet hemomycin so that adsorption of luteinizing hormone from the sample onto the membrane is substantially reduced;
   (c) subjecting about 5 to 50 ml of the clarified urine sample to absorbent induced ultrafiltration through an ultrafiltration membrane having a molecular weight cut-off from about 5,000 to about 50,000, whereby luteinizing hormone is retained in the sample;
   (d) continuing the ultrafiltration until the retentate sample is concentrated to one-tenth to one-five hundredth its original volume;
   (e) diluting the retentate sample with sufficient water to provide a retentate sample of about 0.5 ml; and
   (f) contacting the retentate sample with the appropriate amount of an immunological reagent for detecting the presence of luteinizing hormone in the retentate sample.

2. The method of claim 1 in which the luteinizing hormone is detected by a luteinizing hormone antiserum or a human chorionic gonadotropin antiserum which cross reacts with luteinizing hormone.

3. A method for detecting follicle stimulating hormone or human menopausal gonadotropin in urine at a concentration of 15 or more m.I.U./ml of urine, which comprises:
   (a) clarifying a sample of the urine to be tested;
   (b) contacting the urine sample before, during or after clarification with 0.1 to 5% aqueous solution of a protein selected from the group consisting of bovine serum albumin, rabbit serum albumin, human serum albumin, gamma globulin, myoglobin, fibrinogen, human hemoglobin, and keyhold limpet hemomycin so that adsorption of follicle-stimulating hormone or human menopausal gonadotropin from the sample onto the membrane is substantially reduced;
   (c) subjecting about 5 to 50 ml of the clarified urine sample to absorbent induced ultrafiltration through an ultrafiltration membrane having a molecular weight cut-off from about 5,000 to about 50,000, whereby follicle-stimulating hormone or human menopausal gonadotropin is retained in the sample;
   (d) continuing the ultrafiltration until the retentate sample is one-tenth to one-five hundredth its original volume;
   (e) diluting the retentate sample with sufficient water to provide a retentate sample of about 0.5 ml; and
   (f) contacting the retentate sample with the appropriate amount of an immunological reagent for detecting the presence of follicle-stimulating hormone or human menopausal gonadotropin.

4. A test method suitable for detection of pituitary gonadotropins in urine at a concentration as low as about 15 m.I.U./ml of urine which comprises:
   (a) clarifying a sample of the urine to be tested;
   (b) subjecting about 5 to 50 ml of the clarified urine sample to absorbent induced ultrafiltration through an ultrafiltration membrane, said membrane having been prewashed with 0.1 to 5% aqueous solution of a protein selected from the group consisting of bovine serum albumin, rabbit serum albumin, human serum albumin, gamma globulin, myoglogin, fibrinogen, human hemoglobin, and keyhold limpet hemocyanin so that adsorption of the gonadotropin from the sample onto the membrane is substantially reduced, and said membrane having a molecular weight cut-off from about 5,000 to about 50,000 whereby the gonadotropin is retained in the sample;
   (c) continuing the ultrafiltration until the retentate sample is one-tenth to one-five hundredth its original volume;
   (d) diluting the retentate sample with sufficient water to provide a retentate sample of about 0.5 ml; and
   (e) contacting the retentate sample with the appropriate amount of an immunological reagent for detecting the presence of the gonadotropin in the retentate sample.

5. The method of claim 4 wherein said ultrafiltration membrane is of the anisotropic type and in which the membrane has a molecular cut-off from about 10,000 to about 35,000.

6. The method of claim 4, wherein said ultrafiltration membrane is of the anisotropic type and the concentration of said solution of protein is from 0.1 to 1.0%.

7. The method of claim 4 wherein said clarifying step comprises filtration through a filter and which further comprises prewashing said filter with the aqueous solution of a protein.

8. A test method suitable for detection of pituitary gonadotropins in urine at a concentration as low as about 15 m.I.U./ml of urine which comprises:
   (a) clarifying a sample of the urine to be tested;
   (b) contacting the urine sample before or after clarification with a sufficient amount of a protein selected from the group consisting of bovine serum albumin, rabbit serum albumin, human serum albumin, gamma globulin, myoglobin, fibrinogen, human hemoglobin, and keyhold limpet hemocyanin to give a concentration of the protein in the urine of from 0.001 to 1.0% so that adsorption of the gonadotropin from the sample onto the membrane is substantially reduced;
   (c) subjecting about 5 to 50 ml of the clarified urine sample to absorbent induced ultrafiltration through an ultrafiltration membrane having a molecular weight cut-off from about 5,000 to about 50,000 whereby the gonadotropin is retained in the sample;
   (d) continuing the ultrafiltration until the retentate sample is one-tenth to one-five hundredth its original volume;
   (e) diluting the retentate sample with sufficient water to provide a retentate sample of about 0.5 ml; and
   (f) contacting the retentate sample with the appropriate amount of an immunological reagent for detecting the presence of the gonadotropin in the retentate sample.

9. The method of claim 8 wherein said membrane is of the anisotropic type, said membrane being backed by a layer of absorbent capable of sorbing urine.

10. The method of claim 9 wherein the concentration of said protein in the urine is from 0.01 to 1.0%.

11. A test method suitable for detection of pituitary gonadotropins in urine at a concentration as low as about 15 m.I.U./ml of urine, which comprises:
  (a) clarifying a sample of the urine to be tested through a filter, said filter having been pretreated with an 0.1 to 5.0% aqueous solution of a protein selected from the group consisting of bovine serum albumin, rabbit serum albumin, human serum albumin, gamma globulin, myoglobin, fibrinogen, human hemoglobin, and keyhold limpet hemocyanin so that adsorption of the gonadotropin from the sample onto the membrane is substantially reduced;
  (b) subjecting about 5 to 50 ml of the clarified urine sample to absorbent induced ultrafiltration through an ultrafiltration membrane having a molecular weight cut-off from about 5,000 to about 50,000, whereby the gonadotropin is retained in the sample;
  (c) continuing the ultrafiltration until the retentate sample is one-tenth to one-five hundredth its original volume;
  (d) diluting the retentate sample with sufficient water to provide a retentate sample of about 0.5 ml; and
  (e) contacting the retentate sample with the appropriate amount of an immunological reagent for detecting the presence of the gonadotropin in the retentate sample.

12. The method of claim 11 in which said membrane is of the anisotropic type having a molecular weight cut-off from about 10,000 to about 35,000 and wherein the concentration of said solution of protein is from 0.1 to 1.0%.

* * * * *